United States Patent [19]

Gould

[11] Patent Number: 5,054,327

[45] Date of Patent: * Oct. 8, 1991

[54] APPARATUS FOR AUDITING MEANS USED FOR MEASURING AN ALIQUOT FROM A BULK MATERIAL FOR MEASUREMENT OF ONE OR MORE CHARACTERISTICS OF SAID BULK MATERIAL

[76] Inventor: Gregory Gould, 30 Clairmont Ave., Thornwood, N.Y. 10594

[ * ] Notice: The portion of the term of this patent subsequent to Nov. 28, 2006 has been disclaimed.

[21] Appl. No.: 587,821

[22] Filed: Sep. 24, 1990

Related U.S. Application Data

[60] Division of Ser. No. 415,943, Oct. 2, 1989, which is a continuation-in-part of Ser. No. 144,995, Jan. 19, 1988, Pat. No. 4,882,927.

[51] Int. Cl.$^5$ ............................................. G01D 18/00
[52] U.S. Cl. ..................................................... 73/863
[58] Field of Search ............... 73/1 R, 1 B, 1 H, 32 R, 73/866, 866.5, 433, 863, 864, 864.81–864.87, 73; 422/68.1; 364/497, 498, 499, 567, 571.01–571.08; 177/50; 374/36

[56] References Cited

U.S. PATENT DOCUMENTS

| | | | |
|---|---|---|---|
| 4,250,257 | 2/1981 | Lee et al. | 436/169 X |
| 4,324,146 | 4/1982 | Born | 73/863.12 |
| 4,882,927 | 11/1989 | Gould | 73/1 R |
| 4,954,975 | 9/1990 | Kalata | 364/571.01 X |
| 4,969,115 | 11/1990 | Rosenthal | 364/498 X |

Primary Examiner—Tom Noland
Attorney, Agent, or Firm—John L. Gray

[57] ABSTRACT

This invention concerns a method and an apparatus for auditing the means used for extracting an aliquot of a bulk material from its mass for measurement of one or more characteristics of said bulk material, especially during handling or processing, and involves concurrently measuring one or more variables which affect the accuracy or the reliability of said means used for making the extraction to produce an aliquot with the same characteristics as the mass from which the extraction was made.

48 Claims, 2 Drawing Sheets

APPARATUS FOR AUDITING MEANS USED FOR MEASURING AN ALIQUOT FROM A BULK MATERIAL FOR MEASUREMENT OF ONE OR MORE CHARACTERISTICS OF SAID BULK MATERIAL

This application is a division of application Ser. No. 07/415,943 filed Oct. 2, 1989 which application is a continuation-in-part application to Ser. No. 144,995, Gould, filed Jan. 19, 1988, and now is U.S. Pat. No. 4,882,927, Gould, issued Nov. 28, 1989.

BACKGROUND OF THE INVENTION

This patent application is related to co-pending U.S. patent application Ser. No. 144,995 filed Jan. 19, 1988 and now U.S. Pat. No. 4,882,927 entitled Method And Apparatus For Auditing Means Used For Measuring Characteristics Of A Bulk Material. Bulk materials such as bauxite, elemental sulphur, phosphates, gypsum, limestone, cement, iron ore, iron ore pellets, corn, wheat, and other grains, sugar, coal, lignite, peat, anthracite, waste products, sewage sludge, wood chips and bark, and paper regularly have various characteristics measured, especially during handling or processing, by means of extracting an aliquot that is intended to accurately contain every variable constituent present in the mass of said material in the same proportions and in the same physical and chemical state as said constituents exist in the mass of said material, and measuring said characteristics of said aliquot.

The value of these goods in the United States is enormous. For example, the forest products group, which is in Standard Industrial Class 26, had a total value of shipments in 1986 of about $108 billion. Of this amount, pulp mills accounted for $4.1 billion, paper and board mills $42 billion, newspapers $23 billion, corrugated and solid fiber boxes $14 billion, sanitary paper products $11 billion, and sanitary food containers $3 billion. Coal is another bulk material which regularly has various of its characteristics measured, and in 1986 the forecast was for approximately $30 billion of coal to be mined and processed in the United States.

Among other bulk materials, nitrogenous and phosphatic fertilizers account for about $9 billion annually. Primary metals account for $50 to $60 billion and inorganic chemicals about $12 billion. In 1986 there was about $4 billion worth of cement produced in the United States.

Unfortunately in handling and processing such bulk materials, significant errors arise with respect to extraction of aliquots on which measurements of said characteristics are made.

As an example, coal is produced in the United States in about 5,000 mines operated by about 3,000 companies. Approximately 85 percent of total coal produced annually in the United States is consumed by the electric utility industry amounting to about $22.9 billion. Electric utility inventories are currently approximately 163 million tons with a nominal value of $5.5 billion.

The electric utility industry writes off up to five percent of inventories annually because of their inability to reconcile the value of the coal purchased with the value of the coal burned. This corresponds to an annual write off of this product alone of $273 million. Since coal is essentially nonperishable in the ordinary time frames associated with the commerce of coal, such losses for the most part do not represent physical losses but rather inaccuracies in weighing, sampling and analyzing.

There are significant economic ramifications far beyond simple inventory corrections. For example, inaccuracies resulting in overstatement of actual thermal content must be compensated for by carrying an increment of extra inventory in order to be safe. The cost of purchase, stocking, interest, and insurance are very real though undefinable lacking more accurate figures. Additional economic ramifications are related to more accurate and timely quality information. The economic impact of forced derating of units and associated purchase of outside power, losses associated with less than ideal economic dispatch, and operation with coal quality better than actually needed to meet air quality regulations are examples. Again, such economic losses cannot easily be estimated lacking more accurate and timely information; however, they are substantial. The same problems arise in other bulk materials industries which in dollar volume far exceeds that of coal.

There is a substantial need for sampling and weighing at bulk terminals through which bulk materials move, both in import and export markets. The United States produced about $4 billion worth of cement in 1986 and imported cement worth about $300 million. The value of metal and mineral mining shipments in Standard Industrial Classifications 10 and 14, which excludes fuels, was $23 billion in 1986. Imports amounted to $3.2 billion. The coal industry exported 88 million tons with the value estimated to be $3.5 billion.

SUMMARY OF THE INVENTION

This invention involves a method and apparatus of auditing and documenting operational and environmental variables or manifestations of such variables which can influence the accuracy and reliability of means used for extracting an aliquot of bulk material, which said aliquot is intended to accurately contain every variable constituent present in the mass of said bulk material in the same proportions and in the same physical and chemical state as said constituents exist in the mass of said bulk material from which said aliquot was extracted, to authenticate that the accuracy and reliability of said aliquot has not been impaired by variables which may affect the accuracy and reliability of said means of extracting said aliquot. In doing this it is very useful concurrently to compare said operational and environmental variables with appropriate references.

It is therefore an object of this invention to provide a method and equipment to authenticate the accuracy and reliability of the means of extracting said aliquot.

It is a further object of this invention to provide such method and apparatus which will enable said measured operational and environmental variables to be concurrently compared with one or more appropriate references.

The monitoring of operational variables and comparison with the appropriate references affords means for enhanced closed-loop control of operations within preselected limits beyond that afforded by bin level, plugged chute, and flow sensing controls, and for annunciating out of limit conditions which may require human intervention for correction or adjustment.

It is therefore an additional object of this invention to provide means for enhanced closed-loop control and annunciating out of limit operational conditions which may require human intervention for correction or adjustment.

These, together with other objects and advantages of the invention will become more readily apparent to those skilled in the art when the following general statements and descriptions are read in the light of the appended drawings.

DETAILED DESCRIPTION OF INVENTION

While this invention has been described with particular application of its use in the handling of coal in an electric utility, it should be kept in mind that it has equal application to other bulk materials as enumerated hereinabove.

It should also be understood that all of the components, except for the software for a particular installation, are off-the-shelf items that are readily available at the present time.

Figure 1:
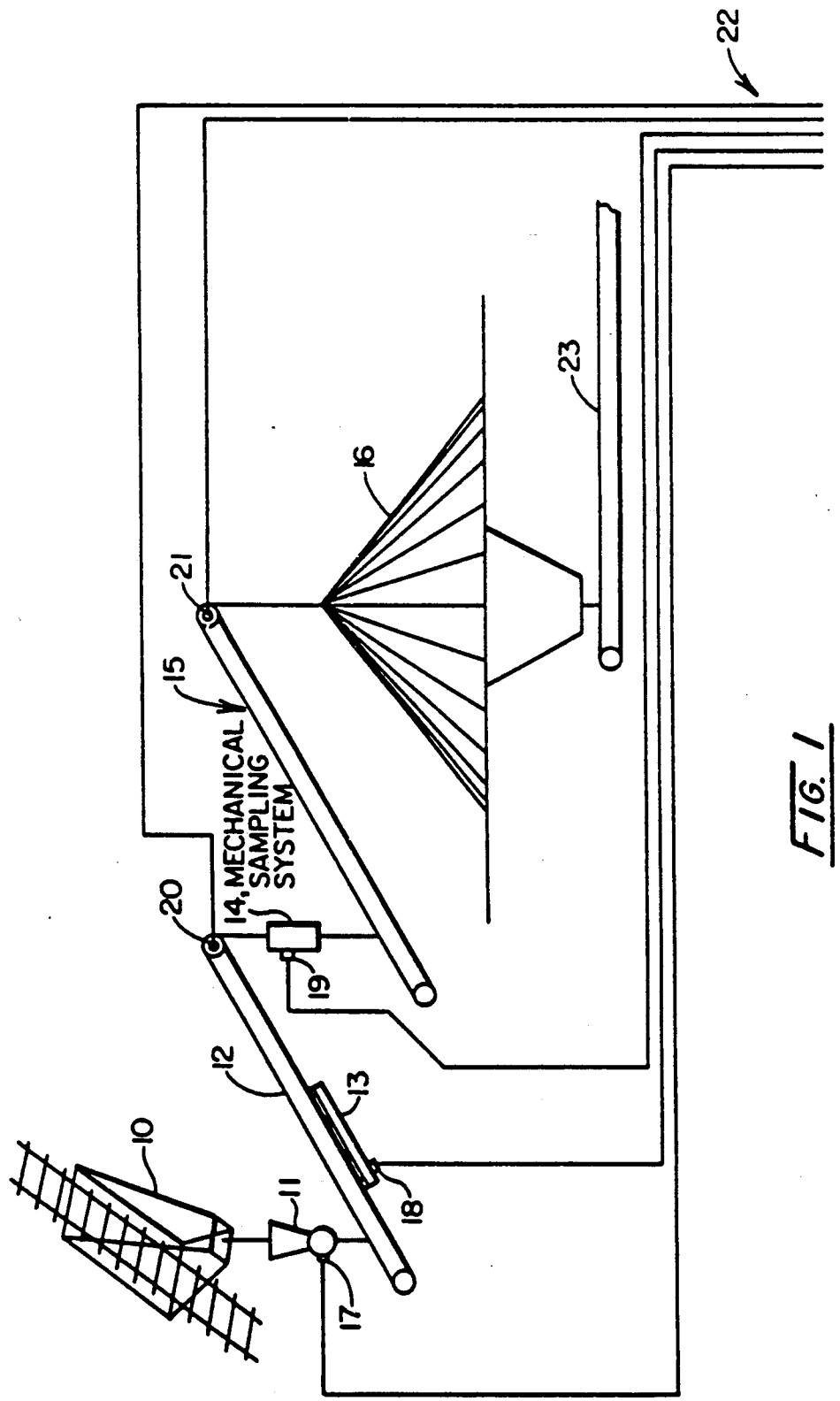
FIG. 1 is a schematic view of the invention as applied to the handling of coal from its receipt in a hopper car to storage in a stockpile in a handling system that includes both weighing and machine sampling facilities.

Referring now to the drawings and particularly to FIG. 1, item 10 represents a rail siding track hopper unloading facility. Coal moves from the track hopper shown at 10 to a crusher 11 and thence to a belt 12 moving over a belt scale 13 and thus to a mechanical sampling system 14. From here the coal which is not removed in the mechanical sampling system 14 is carried upward on belt 15 and then discharged into storage pile 16. Track hopper 10 is typically equipped with a coarse screen referred to as a "grizzly" with openings about a foot square to prevent oversize lumps and large frozen masses of coal from becoming lodged in the system. Such lumps are broken down either manually or with special machines called "crackers". While the track hopper 10 is shown discharging directly into crusher 11 for simplification in explaining applicant's invention, in actual practice the coal flow from the tracker hopper 10 would be controlled by means of feeder conveyors.

Generally the facilities and equipment around an electric generating plant are designed to handle coal of nominally two inches top size. The main purpose of crusher 11 is to reduce the coal top size to meet this working requirement. The belt scale 13 represents a certified commercial scale. This means that the weights obtained from it are used for purposes of payment to the coal supplier. Sensors are located at 17 on crusher 11, 18 on belt scale 13, 19 on the mechanical sampling system 14, and 20 on belt conveyor 12. These sensors comprise one or more specific sensors as will be hereinafter described and are connected by means of input-output electrical channels 22—22 to the appropriate recording and monitoring devices shown in FIG. 3.

The commerce of coal is traditionally conducted on an "as received" (wet) basis analysis. This practice is the source of many disputes between buyer and seller. The moisture constituent is subject to loss by drainage and evaporation and gains from precipitation in the form of rain or snow and from water sprays used for dust abatement. In northern climates frozen coal is a constant problem. Blockages frequently occur when wet, unfrozen coal comes in contact with metal surfaces that are below freezing temperature. Sensors at 17, 18, 19, and 20 are used to monitor and permanently record in real time with date and time stamps, ambient environmental temperature, and metal temperatures for crusher 11 and connecting chutes, belt scale 13, mechanical sampling system 14, and connecting chutes, as well as relative humidity for crusher and mechanical sampling system 14. These data authenticate temperature and humidity conditions for reliable and accurate operation of sampling and weighing systems and permit setting alarms for conditions that are likely to cause operational problems or malfunctions of equipment.

Bulk commodities like coal occasionally are contaminated with adventitious materials that can be harmful to equipment. With coal, precautions are needed for everything from blasting caps to broken rail car parts. Magnetic separators are generally installed as early in a coal handling system as possible to protect the machinery from tramp iron. Despite precautions, such adventitious materials occasionally damage moving machinery. Sensors at 17, 18, and 19 are used to monitor and permanently record in real time with date and time stamps, vibration and acoustic levels and patterns for crusher 11, belt scale 13, and mechanical sampling system 14 to authenticate operating conditions for reliable accurate operation of the sampling system 14. This additionally provides means for detecting and annunciating excessive or unusual conditions that might impair extraction of the aliquot or indicate operational problems and possible malfunctions of sampling equipment. There is no clear boundary between audio frequencies and mechanical vibrations but generally mechanical vibrations associated with heavy machinery are below audio frequencies, so amplitudes and frequency patterns of both are monitored and permanently recorded, and compared with appropriate references. This also permits detection of physical abuse by operating personnel when passage of coal is impeded.

In addition, one or more voltage, current, power and motor temperature variables are monitored and recorded in real time with date and time stamps to authenticate operating conditions for reliable operation of crushers and sampling machines with sensors at 11, and 14. This additionally provides means for detecting excessive or unusual conditions that might impair extraction of said aliquot and permits setting alarms for conditions that indicate operational problems and possible malfunctions of equipment. It offers diagnostic opportunities for trouble shooting malfunctions as well.

Figure 2:
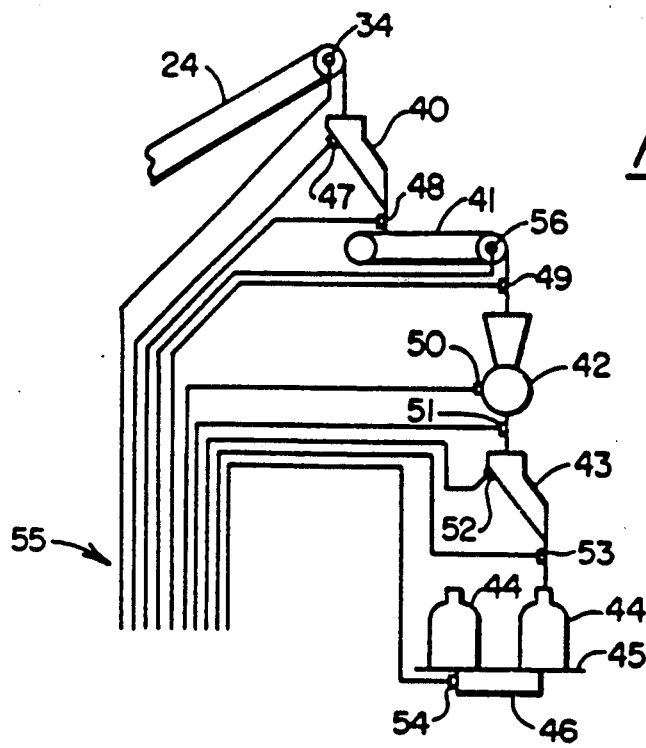
FIG. 2 is an enlarged schematic detail of the treatment of coal in typical mechanical sampling systems shown in FIG. 1.

Referring now more particularly to FIG. 2, there is depicted a detail of a typical sampling machine 14. Shown schematically is a typical two stage mechanical sampling system. This consists of a primary cutter 40, a primary feeder 41, a sample crusher 42, a secondary cutter 43, sample receivers 44—44, sample carousal 45, and sample scale 46. Appropriate chutes connect the various components and directs the coal through the sampling system. Three stage systems that include an additional stage of division, and sometimes an additional state of crushing, are not uncommon.

The handling properties of bulk materials vary with particle size distribution, moisture content and proportion of impurities, and mass flow rate. Coal is among the most intractable of all bulk materials. This situation is exacerbated by on-line crushing and division within the sampling system that alters the handling properties of the material and reduces mass flow rates in the divided sample to the point where friction, adhesion, and cohesion forces tend to override the inertial and gravitational forces that keep the coal in motion.

Blockages, hang-ups, irregular and discontinuous flows are potentially serious sources of error in the extracted aliquot. Physical abuse of sampling systems often occurs when such conditions are encountered. Operating personnel are moved to hammer on the chute work, cutters and crushers with heavy pipes and sledge hammers to restore flow. Such abuse can permanently impair the performance of a sampling system.

Sensors located at 47, 48, 49, 50, 51, 52, 53, and 54 are used to monitor, compare with appropriate references, and permanently record in real time with date and time stamps metal temperature, vibration and audio frequency amplitudes and patterns in connecting chutes, component and component enclosures at sensors 47, 48, 49, 50, 51, 52, 53 and 54 and sample carousel 45 and sample scale 46 to document and authenticate operating conditions for reliable, accurate extracting of the aforesaid aliquot. This surveillance permits setting alarms for conditions that indicate operational problems and possible malfunctioning of equipment or abuse and affords diagnostic opportunities for trouble shooting and malfunctions as well. These sensors comprise one or more specific sensors as will be hereinafter described and are connected by means of input-output electrical channels 55—55 to the appropriate recording and monitoring devices shown in FIG. 3.

There are two basic methodologies generally employed in aliquot extraction from bulk materials, time basis and mass basis. For both types of sampling, national and international standards prescribe the minimum number and minimum mass of increments required relative to mass of the lot or consignment to be represented by the aliquot.

Time basis sampling extracts a sample increment at uniformly spaced time intervals. In order to maintain the same proportion of variable constituents in the aliquot as exists in the whole, the sample cutters which extract the aliquot, must move at a fixed velocity the same for every increment.

Mass basis sampling extracts a sample increment at uniformly spaced mass intervals and the velocity of sample cutters must vary in direct proportion to variations in flow rate in order to maintain the same proportion of the variable constituents in the aliquot as exists in the whole.

With both time basis and mass basis sampling, serious error can accrue if cutter traverses occur in synchronization with linear variations in quality, relative to time or mass, or if secondary or tertiary cutter traverses occur in synchronization with preceding cutters in the system.

Linear variations in quality relative to time or mass are frequently related to variations in flow rate which in turn may reflect materials handling system capacity limitations associated with changing handling properties of the bulk material. Crushers also induce linear variations in quality relative to time or mass that is attributable to crushing of easier to crush material first.

Thus to authenticate operating conditions for accurate reliable time and mass basis aliquot extraction, sensors located at 47, 52, and 56 are used to count the number of traverses of the primary cutter 40 and the secondary cutter 43 and to measure the speed of the primary feeder 41, and 5 to measure and record in real time with date and time stamps the time at which traverses occurred, length of traverse cycle, the velocity of sample cutters for every traverse, and to determine whether cutters are operating in synchronization. This surveillance additionally permits setting alarms for conditions that indicate operational problems and possible malfunctioning of equipment and, of course, diagnostic opportunities for trouble shooting malfunctions as they occur.

Sensors located at 18 are used to monitor and permanently record in real time with date and time stamps the flow rate, voltage, and current (or power) of the power supply, ambient temperature, vibrations amplitudes and patterns, and operating times of belt scales 13, and to authenticate the flow rates to sample system 14, and to cross check synchronization of flow variations and flow discontinuities with cutter traverses.

Sensors located at 20, 21 in FIG. 1, and 34, 56 in FIG. 2, are used to monitor and permanently record in real time with date and time stamps conveyor speed, voltage and current (or power) to conveyor drive motors, or motors of hydraulic power packs for detecting fault conditions on conveyors 12, 15 and 24, 41.

All conveyors of modern bulk materials handling systems are interlocked to prevent operation of any conveyor preceding another in the system which is not operating For this reason, sensors to monitor the status of the existing controls is a viable alternative to the sensors mentioned above recording information with respect to conveyor speed, voltage, etc., if no redundancy in sensors is deemed necessary.

Aliquot extraction of bulk materials is a complex demanding task for which the need for accuracy and reliability has not achieved the same broad recognition in society in general as has weighing. As a result, no similar legal or regulatory certification requirements exist. There are, however, national and international voluntary consensus standards that are widely used in commerce by reference in contracts and agreements.

Figure 3:
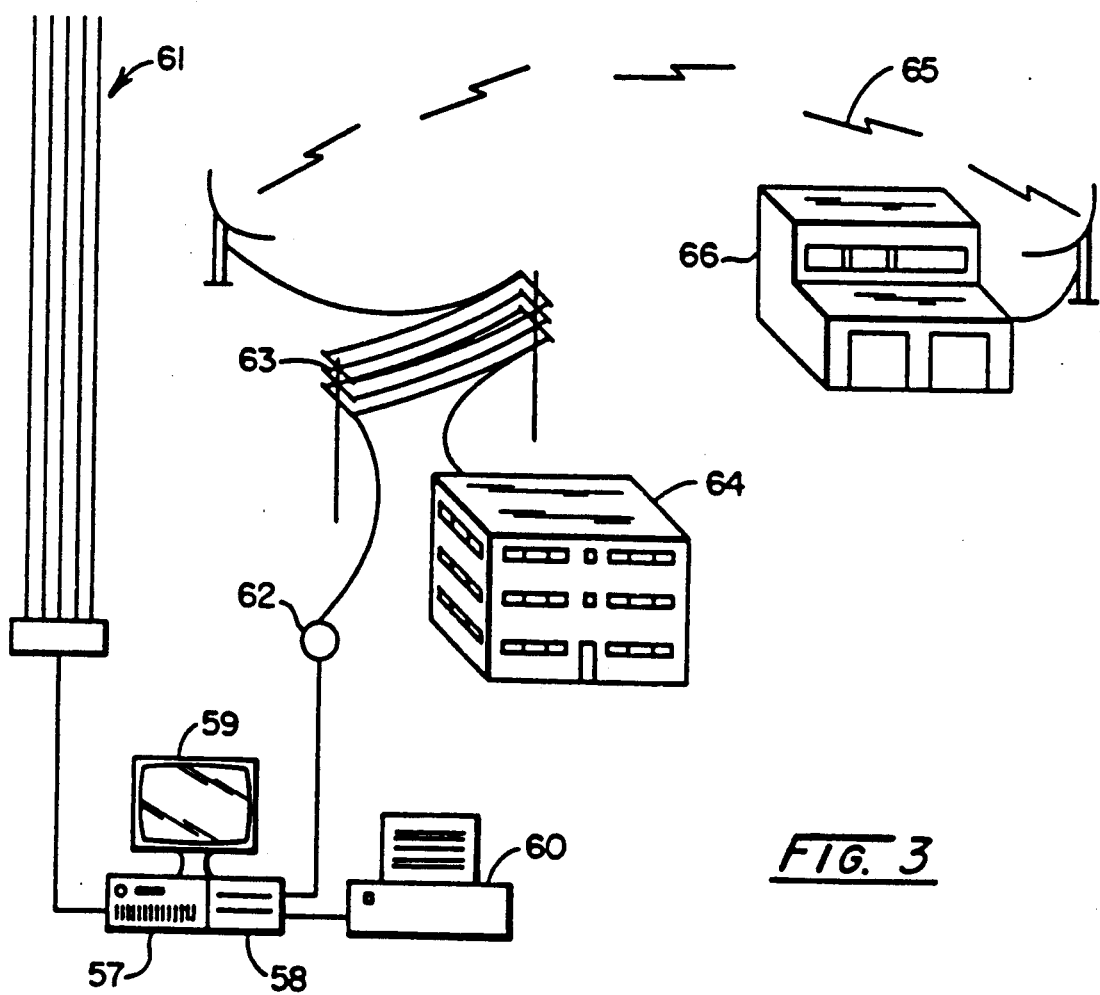
FIG. 3 schematically depicts the computer software and peripherals employed in this invention for receiving, storing and analyzing data obtained from the various sensors utilized in the system which signal and record and maintain a data base of conditions of operations, malfunctions, and failures, and reporting status of bulk materials, receipts, use and inventory, locally and remotely, on video monitors and printed copy, and interfacing with main frame computers.

Referring now more particularly to FIG. 3, there is shown a computer 57 provided with disc drive system 58, and one or more video terminals 59, one or more printers 60, connected by input-output electrical channel 61 to the corresponding conduits shown in FIGS. 1 and 2, from the sensors. Also shown is modem 62, telephone link 63 to a main office 64, and a microwave link 65 to a central repair shop 66. Computer 57 is controlled by proprietary software that polls the various sensors in the system through multiple analog and digital input-output channels which condition the incoming signals. Computer 57 is equipped with an electronic clock calendar, disc drives for permanently recording data from the sensors, and necessary interfaces for modem, printer, and video terminal keyboard.

The software performs many services. It converts sensor signals into real world units, if necessary, directs the permanent recording of the sensor data in a database maintained on disc drive system 58, with date and time stamps from the internal electronic clock calendar, analyzes the sensor data for status relative to predesignated benchmark references, checks for cutter synchronization conditions, and activates visual and audible alarms for any conditions outside predesignated limits, or requiring human attention or intervention.

For comparing the data against predesignated benchmark references, appropriate references can be selected. For example: Such benchmarks include contract, equipment, and process specifications, operating and material standards, purchase and acceptance specifications, regulatory and legal limits, and experience and empirically established limits.

The software provides the necessary services for interactive keyboard input of biographical data, and maintains access security to various levels of the software and data by predesignated priority levels. The software generates interruption, failure, status, operations and diagnostic reports, locally and at remote terminals in the main office and repair shop. The software also provides for inputs and outputs to mainframe computers.

The implementation of this invention is site specific and must be customized to the particular needs of any given facility. It is desirable that the computer program instruction code be modular reentrant code to facilitate this kind of customization. Such computer programs are readily prepared by qualified programmers familiar with structured assembly or higher level computer languages.

While this invention has been described in its preferred embodiment, it is to be appreciated that variations therefrom may be made without departing from the true scope and spirit of the invention.

What is claimed:

1. Apparatus for auditing for accuracy or reliability a means used for extracting an aliquot from a bulk material which comprises a first means for extracting an aliquot from said bulk materials and a second means for concurrently measuring one or more variables which directly or indirectly affect the normal operation of said first means and thereby affect the accuracy or reliability of the extraction of said aliquot by said first means, which variables are independent of said first means for extracting said aliquot from said bulk material.

2. The apparatus of claim 1 which comprises a third means for comparing the measurements obtained by said second means with an appropriate reference.

3. The apparatus of claim 1 wherein said second means includes means for measuring manifestations of said variables.

4. The apparatus of claim 1 wherein said second includes a scale.

5. The apparatus of claim 1 wherein said second means includes means for measuring bulk density.

6. The apparatus of claim 1 wherein said second means includes means for measuring the chemical composition of said bulk material.

7. The apparatus of claim 1 wherein said second means includes means for measuring constituent composition of said bulk material.

8. The apparatus of claim 1 wherein said second means includes means for measuring the moisture content of said bulk material.

9. The apparatus of claim 1 wherein said second means includes means for measuring an attribute of one or more constituents of said bulk material.

10. The apparatus of claim 9 wherein said means for measuring an attribute of one or more constituents of said bulk material comprises means for measuring the heating value of the combustible constituents of said bulk material.

11. The apparatus of claim 1 wherein said second means includes means for measuring ambient air movement.

12. The apparatus of claim 1 wherein said second means includes means for measuring air movement internal to said first means.

13. The apparatus of claim 1 wherein said second means includes means for measuring the temperature of ambient air.

14. The apparatus of claim 1 wherein said second means includes means for measuring fluctuations in temperature of the ambient air.

15. The apparatus of claim 1 wherein said second means includes means for measuring the surface temperatures of said first means.

16. The apparatus of claim 1 wherein said second means includes means for measuring the temperature of said bulk material.

17. The apparatus of claim 1 wherein said second means includes means for measuring relative humidity of the air in contact with said bulk material.

18. The apparatus of claim 1 wherein said second means includes means for measuring dew point.

19. The apparatus of claim 1 wherein said second means includes means for measuring mechanical vibration.

20. The apparatus of claim 1 wherein said second means includes means for measuring levels of mechanical vibrations.

21. The apparatus of claim 1 wherein said second means includes means for measuring acoustical sound levels.

22. The apparatus of claim 1 wherein said second means includes means for measuring changes in acoustical sound patterns.

23. The apparatus of claim 1 wherein said second means includes means for measuring vibration patterns.

24. The apparatus of claim 1 wherein said second means includes means for measuring changes in vibration patterns.

25. The apparatus of claim 1 wherein said second means includes means for measuring flow rate of said bulk material.

26. The apparatus of claim 1 wherein said second means includes means for measuring the pressure within components of said first means.

27. The apparatus of claim 1 wherein said second means includes means for measuring the fluctuations in pressure within components of said first means.

28. The apparatus of claim 1 wherein said second means includes means for measuring electrical voltage supplied to components of said first means.

29. The apparatus of claim 1 wherein said second means includes means for measuring electrical current supplied to components of said first means.

30. The apparatus of claim 1 wherein said second means includes means for measuring fluctuations in voltage supplied to components of said first means.

31. The apparatus of claim 1 wherein said second means includes means for measuring interference from external sources, said external sources selected from the group consisting of electrical, radio frequency, x-ray, gamma ray, atomic and subatomic sources.

32. The apparatus of claim 1 wherein said second means includes means for measuring the timing of operating cycles of said first means.

33. The apparatus of claim 1 wherein said second means includes means for measuring the synchronization of operation cycles of said first means.

34. The apparatus of claim 1 wherein said second means includes means for measuring the speed of rotation of components of said first means.

35. The apparatus of claim 1 wherein said second means includes means for measuring fluctuations in the speed of rotation of components of said first means.

36. The apparatus of claim 1 wherein said second means includes means for measuring the velocity of components of said first means.

37. The apparatus of claim 1 wherein said second means includes means for measuring fluctuations in the velocity of components of said first means.

38. The apparatus of claim 1 wherein said second means includes means for measuring the velocity of said bulk material during the handling of said bulk material and during extraction of said aliquot from said bulk material.

39. The apparatus of claim 1 wherein said second means includes means for measuring the fluctuations in velocity of said bulk material during the handling of said bulk material and during extraction of said aliquot from said bulk material.

40. The apparatus of claim 1 wherein said second means includes means for measuring the position of said first means relative to said bulk material.

41. The apparatus of claim 1 wherein said second means includes means for measuring the alignment of said first means with respect to a reference orientation.

42. The apparatus of claim 1 wherein said second means includes means for measuring the position of said bulk material relative to said first means.

43. The apparatus of claim 1 which comprises a fourth means for preparing date and time stamped permanent records of all measurements made by the second means.

44. The apparatus of claim 1 which comprises a fifth means for displaying the current status of all critical monitored variables and measurements.

45. The apparatus of claim 1 which comprises a sixth means for analyzing and evaluating the relationships among monitored variables and measurements.

46. The apparatus of claim 45 wherein said means for analyzing and evaluating the relationships among monitored variables and measurements is a microprocessor under software control.

47. The apparatus of claim 1 wherein said second means includes means for measuring the fluctuation in moisture content of said bulk material.

48. The apparatus of claim 1 wherein said second means includes means for measuring the fluctuation in level of one or more of the characteristics of said bulk material.

* * * * *